(12) United States Patent
Ridgway et al.

(10) Patent No.: US 8,251,017 B2
(45) Date of Patent: Aug. 28, 2012

(54) BIOME IN A BOX SYSTEM

(76) Inventors: Regina S. Ridgway, Williamsburg, VA (US); Richard V. Bundy, Toano, VA (US)

( * ) Notice: Subject to any disclaimer, the term of this patent is extended or adjusted under 35 U.S.C. 154(b) by 138 days.

(21) Appl. No.: 12/829,817

(22) Filed: Jul. 2, 2010

(65) Prior Publication Data
US 2010/0270195 A1 Oct. 28, 2010

Related U.S. Application Data

(60) Provisional application No. 61/270,088, filed on Jul. 2, 2009, provisional application No. 61/276,205, filed on Sep. 9, 2009.

(51) Int. Cl.
*A01K 1/03* (2006.01)
(52) U.S. Cl. ............................................ 119/452; 47/69
(58) Field of Classification Search .......... 119/245–246, 119/248, 251, 416–417, 452; 47/69
See application file for complete search history.

(56) References Cited

U.S. PATENT DOCUMENTS

| | | | | |
|---|---|---|---|---|
| 3,584,602 A | * | 6/1971 | Stasio | ............................ 119/252 |
| 4,877,336 A | | 10/1989 | Peppiatt | |
| 5,363,801 A | * | 11/1994 | Watters et al. | ................. 119/452 |
| 5,749,320 A | * | 5/1998 | Sydenstricker | ............... 119/253 |
| 6,105,535 A | | 8/2000 | Atamian | |

FOREIGN PATENT DOCUMENTS

| | | |
|---|---|---|
| AU | 737050 | 8/2001 |
| JP | 2008035848 | 2/2008 |
| WO | WO93100080 | 5/1993 |

OTHER PUBLICATIONS

Steve Spangler Science, See Through Compost Kit Item WCOM #250, Jan. 2012. USA. See, http://www.stevespanglerscience.com/product/see-through-compost-kit (attached).
PCT International Search Report, Nov. 17, 2011 (attached).

* cited by examiner

*Primary Examiner* — Rob Swiatek
*Assistant Examiner* — Ebony Evans

(57) ABSTRACT

A biome in a box system comprising a transparent external container having a first size and a top edge and a transparent internal container having a second size configured to fit within the external container. The internal container is for placement of a habitat and has at least one handle configured to hang over and suspend from the top edge of the external container. The system further includes a hinged lid having a side wall extending over the at least one handle and the top edge and a drain assembly under the transparent internal container.

17 Claims, 12 Drawing Sheets

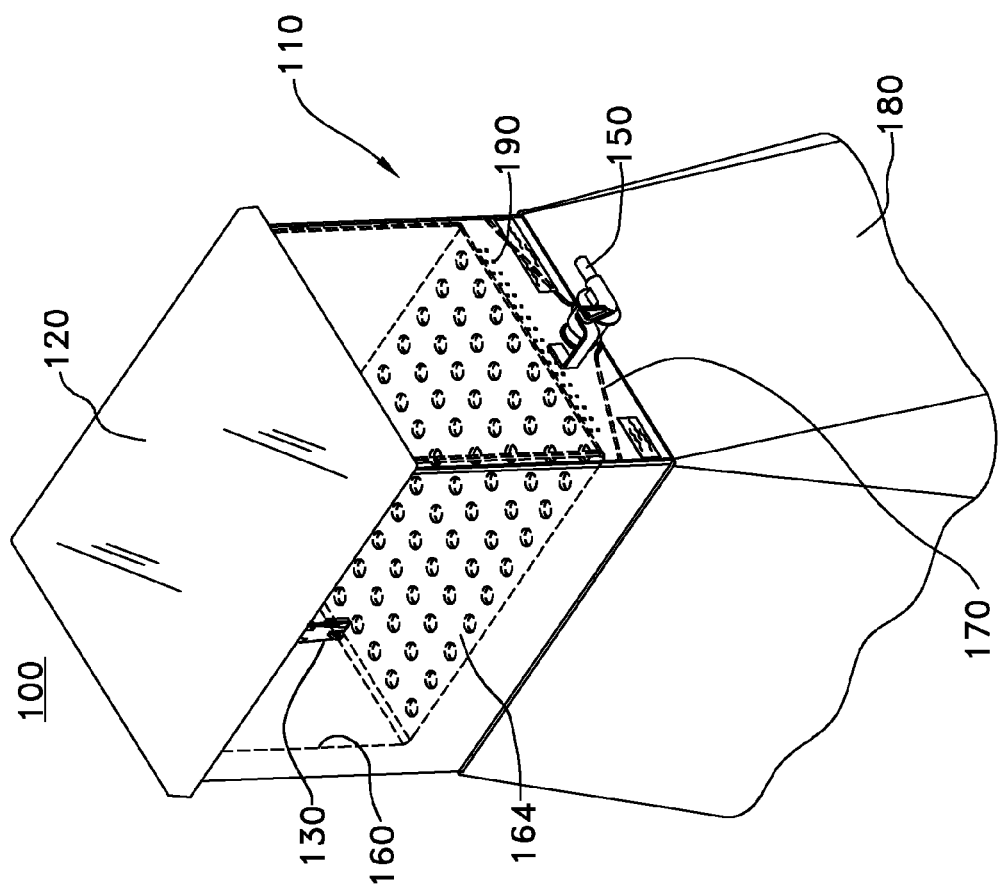

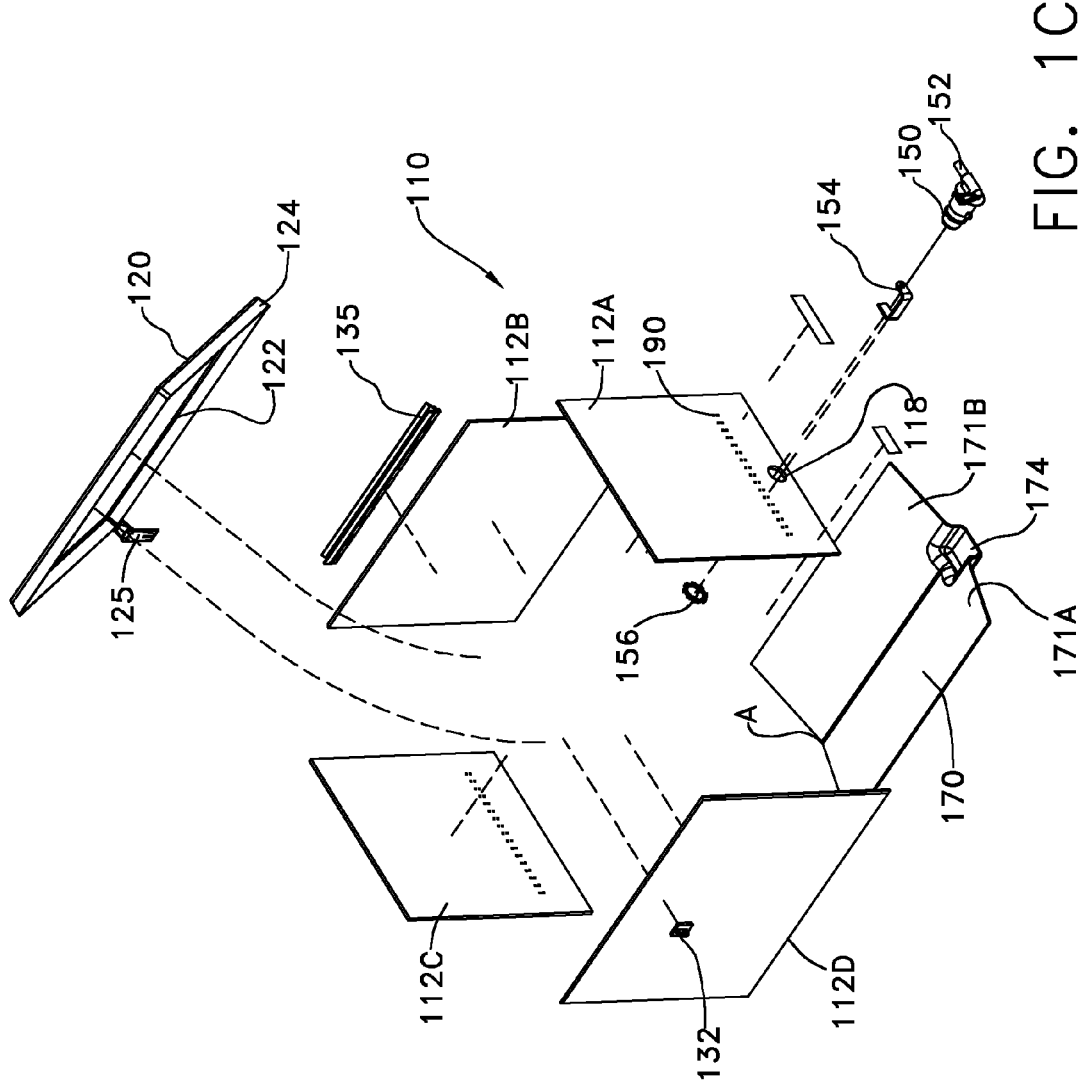

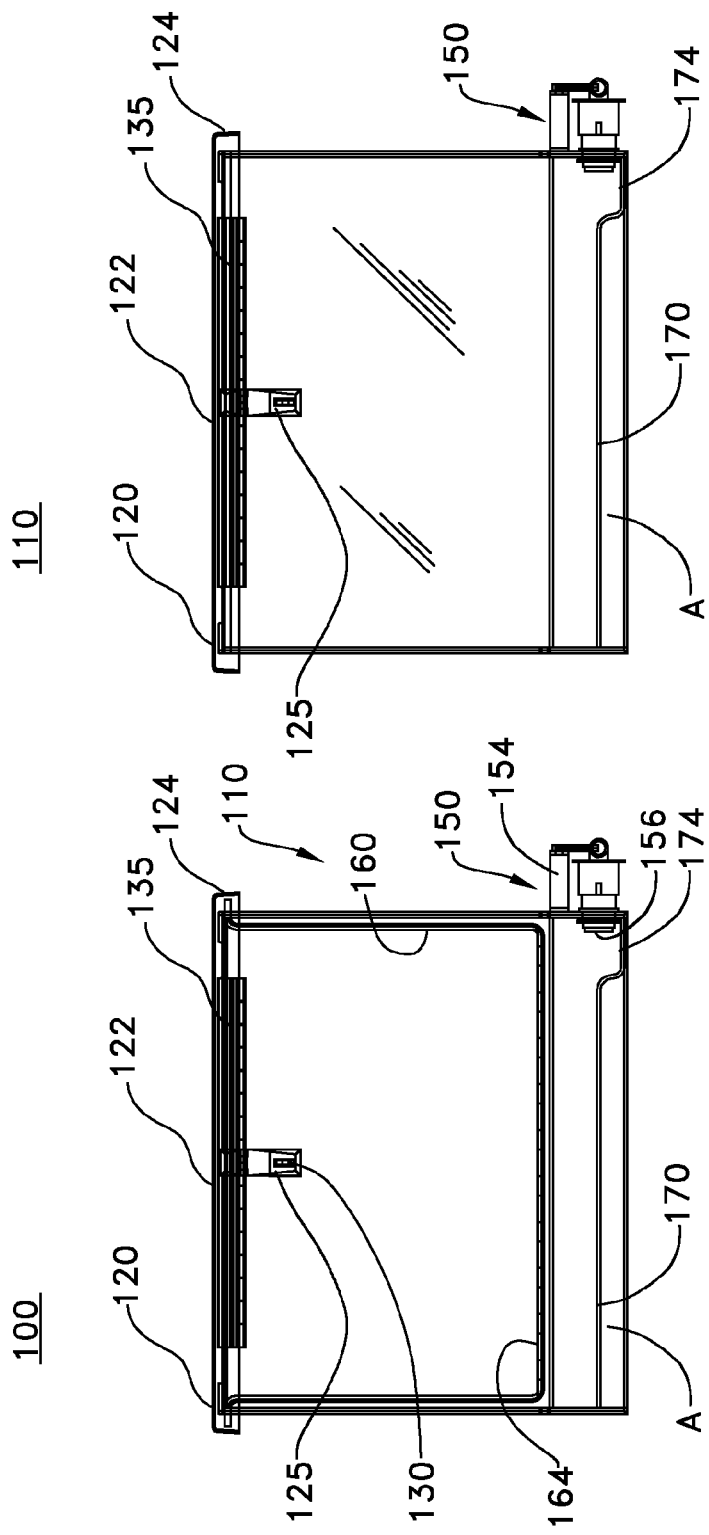

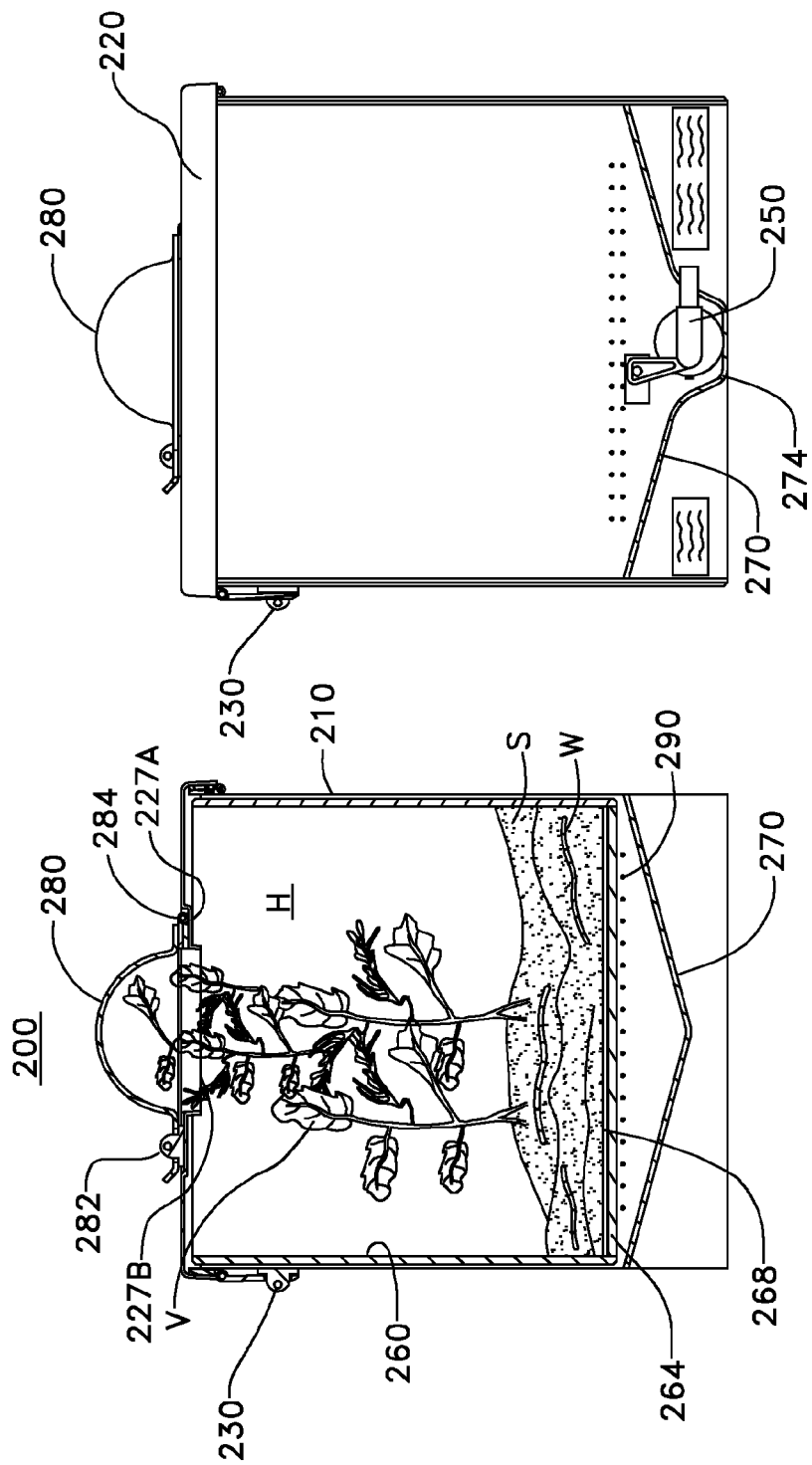

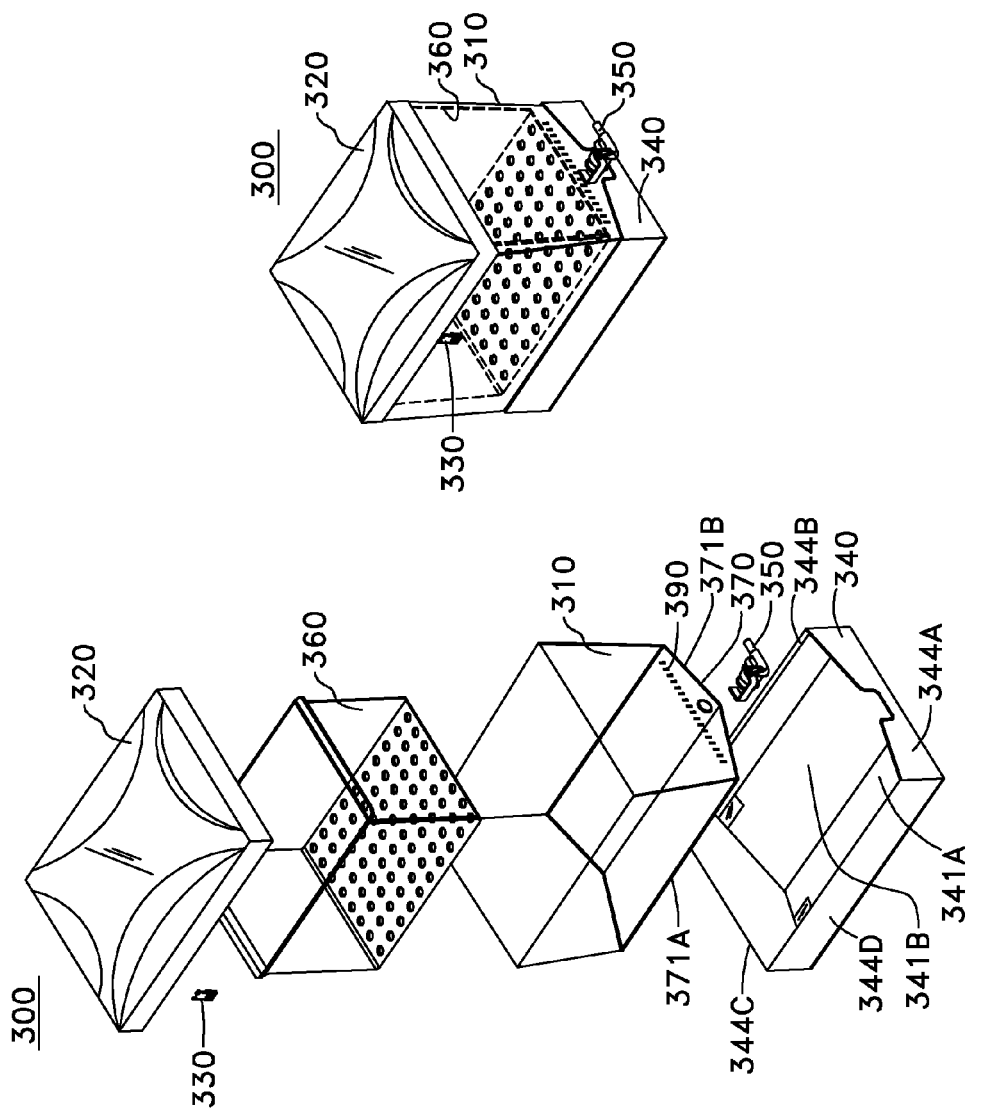

BIOME IN A BOX SYSTEM

COPENDING APPLICATIONS

This application claims priority benefit of Provisional Patent Application No. 61/270,088, filed Jul. 2, 2009, titled "BIOME IN A BOX" having Regina S. Ridgway as inventor and which is incorporated herein by reference as if set forth in full below. This application also claims priority benefit of Provisional Patent Application No. 61/276,205, filed Sep. 9, 2009, titled "COMPOST-BIOME IN A BOX" having the same inventors of the instant patent application and which is incorporated herein by reference as if set forth in full below.

NOTICE OF COPYRIGHT PROTECTION

A portion of the disclosure of this patent document and its figures contain material subject to copyright protection. The copyright owner has no objection to the facsimile reproduction by anyone of the patent document or the patent disclosure, but otherwise reserves all copyrights whatsoever.

BACKGROUND

The invention relates to portable habitats, aquaria, terrariums, biotopes, ecosystems, vermicomposter, composter, tanks, worm tea systems, and containers.

Existing commercial habitat systems, especially composters, have several features that make them difficult to use in a classroom setting. These problematic features include but are not limited to the following: difficulty in continuous observation, open access to the habitat (interior), and difficulty in operation/setup/transport. Existing commercial compost systems have several features which make them difficult to use such as, without limitation, opaque containers, bulkiness, multiple, separate loose components for operation/setup, and open access to the habitat/composter (interior). When the habitats become imbalanced, animals die.

Field educators need to monitor classroom habitats on a continual basis to assure the quality of conditions in the habitat. Container shapes make it difficult for students to observe creatures easily and monitor the stress level of the animals. Since the containers are opaque, the students cannot observe the animals from many angles. In the case of composting systems, the systems are opaque to mimic the dark nature found in soils, so to monitor worms and the health of the composting process, the soil must be dug up to observe the worms which adds stress to the worms.

Additionally, teachers may use rubber/glass/plastic tubs, buckets or pans to demonstrate, collect and display animals. The containers (buckets and pans) are opaque, open, and heavy. Therefore, the buckets and pans tend to be difficult to use as a tool for displaying and transporting creatures back to the classroom. Also these known systems tend to be very heavy and contain multiple components that separate easily and are loosely attached so they are not easily transported from class to class. With limited financial resources, schools/teachers cannot afford to purchase many pieces of equipment for the display, presentation or housing of animals, worms, frogs, or other creatures that require a controlled environment.

The open access of these habitats create several technical challenges with these systems which include but are not limited to contamination through the introduction of chemicals and outside animals, overfeeding, and overwatering in the case of composting. The inability to monitor and protect creatures inside the habitats makes these systems difficult to maintain a healthy environment for animals to thrive. The unsecure interior can be breached where items (e.g., particles, liquids, contaminants, etc.) can be added accidentally that may harm the soil, animals, worms, frogs or other creatures. These systems lack protective features/devices to secure access to the habitat. Teachers are unable to monitor the composter, tanks or terrariums every minute of the day. Some contaminants may be hazardous to the health of the animal, worms, frogs or other creatures.

According to some of the embodiments of this invention, a new design for a classroom/science education product that will simplify teacher responsibilities and promote individual environmental stewardship is provided. The system in accordance with some of the embodiments of this invention include a type of opaque covering (hard or soft) to darken the system devices for security and habitat monitoring purposes, vents for an air circulation and temperature moderation, and/or a drainage system to prevent overfeeding and anoxia (lack of oxygen) due to standing water (found in some composting systems).

SUMMARY

The aforementioned problems, and other problems, are reduced, according to exemplary embodiments, by the biome composting system (also referred to as "Biome in a Box", "BIB" and "biome in a box system") described herein below.

Some of the exemplary embodiments provide a biome in a box system comprising a transparent external container having a first size and shape and a top edge and a transparent internal container having a second size and shape configured to fit within the external container. The internal container is for placement of a habitat and has at least one handle configured to hang over and suspend from the top edge of the external container. The system further includes a hinged lid having a side wall extending over the at least one handle and the top edge and a drain assembly under the transparent internal container.

Additionally, some exemplary embodiments provide a biome in a box system comprising a transparent external container having a top edge and a transparent internal container for placement of a habitat. The internal container has handles configured to hang over and suspend from the top edge of the external container. The system includes a lockable lid having a side wall extending over the at least one handle and the top edge; and a transparent drain assembly having a V-shape. Alternate shapes, such as a U-shape may be used as the drain assembly, and alternate material that is non-transparent may be used for the drain assembly to block observation of any substance being drained. The drain assembly is coupled to the transparent external container at a location under the transparent internal container.

Other systems, methods, and/or products according to embodiments will be or become apparent to one with skill in the art upon review of the following drawings, and further description. It is intended that all such additional systems, methods, and/or products be included within this description, be within the scope of the present invention, and be protected by the accompanying claims.

BRIEF DESCRIPTION OF THE DRAWINGS

The exemplary embodiments, objects, uses, advantages, and novel features are more clearly understood by reference to the following description taken in connection with the accompanying figures wherein:

FIG. 1A illustrates a Biome in a Box (BIB) system in accordance with some exemplary embodiments of the present invention;

FIG. 1C illustrates an exploded view of the external box of the BIB system of FIG. 1A in accordance with some exemplary embodiments of the present invention;

FIG. 1F illustrates a back view of the BIB system of FIG. 1A in accordance with some exemplary embodiments of the present invention;

FIG. 1G illustrates a back view of the external box of the BIB system of FIG. 1A in accordance with some exemplary embodiments of the present invention;

FIG. 2B illustrates an end view of the BIB system of FIG. 2A with a habitat or biome formed therein in accordance with some exemplary embodiments of the present invention;

FIG. 2C illustrates an end view of the BIB system of FIG. 2A in accordance with some exemplary embodiments of the present invention;

FIG. 3A illustrates yet another BIB system in accordance with some exemplary embodiments of the present invention;

FIG. 3B illustrates an exploded view of the BIB system of FIG. 3A in accordance with some exemplary embodiments of the present invention;

DESCRIPTION

Figure 1B:
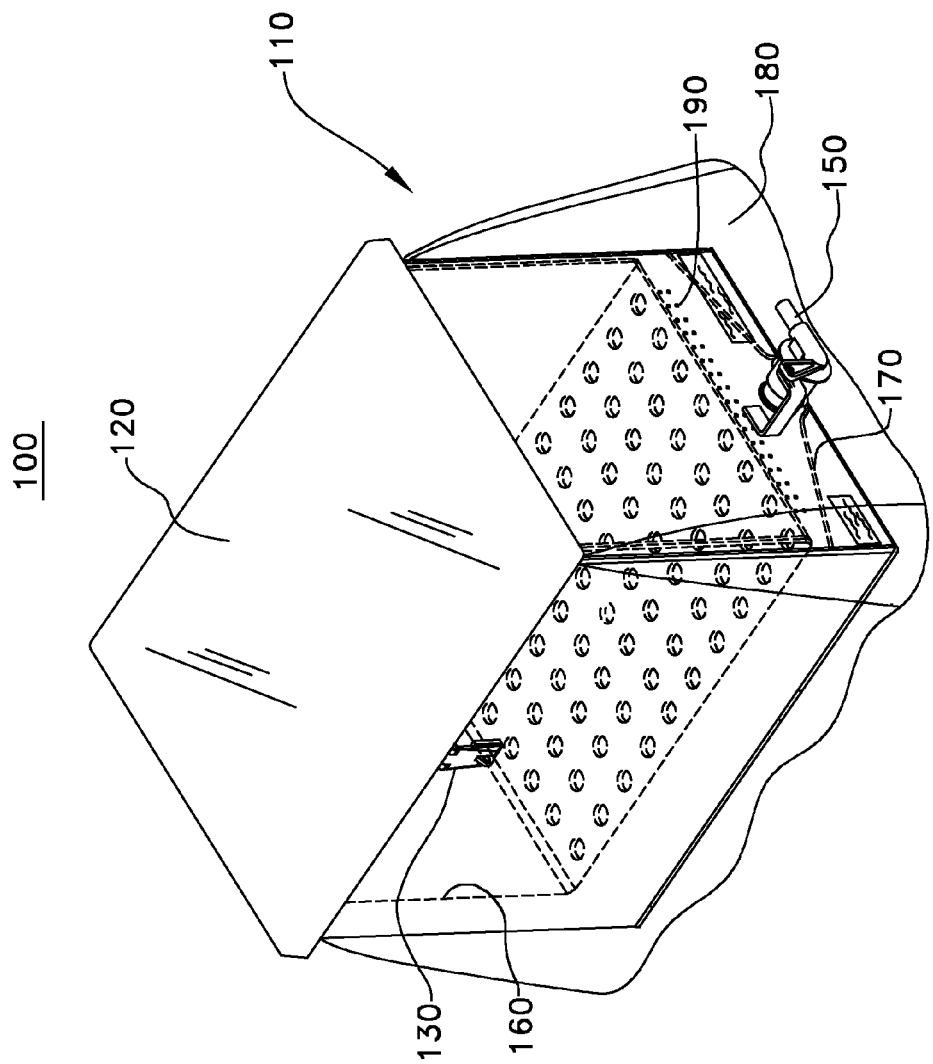
FIG. 1B illustrates a BIB system in a blackout state in accordance with some exemplary embodiments of the present invention.

The word "exemplary" is used herein to mean "serving as an example, instance, or illustration." Any configuration or design described herein as "exemplary" is not necessarily to be construed as preferred or advantageous over other configurations or designs. Furthermore, use of the words "present invention" is used herein to convey only some of the embodiments of the invention. For example, the words "present invention" would also include alternative embodiments and equivalent systems and components that one of ordinary skill the art understands. An example is that the materials used for the exemplary embodiments may be made out of man-made materials, natural materials, and combinations thereof. A further example is that the apparatus or components of the apparatus may be manufactured by machine(s), human(s) and combinations thereof.

Some of the embodiments of the invention now will be described more fully hereinafter with reference to the accompanying drawings, in which exemplary embodiments are shown. This invention may, however, be embodied in many different forms and should not be construed as limited to the embodiments set forth herein. These embodiments are provided so that this disclosure will be thorough and complete and will fully convey the scope of the invention to those of ordinary skill in the art. Moreover, all statements herein reciting embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

FIG. 1A illustrates a Biome in a Box (BIB) system 100 in accordance with some exemplary embodiments of the present invention. The BIB system 100 includes an external box 110, lid 120, internal box 160 (shown in dashed lines) and blackout assembly 180. In the exemplary embodiments, the external box 110 is configured to receive the internal box 160. The lid 120 covers and encloses the top opening of the external box 110 and the top opening of the internal box 160. The lid 120 includes a locking mechanism 130 so that access to the interior of the BIB system 100 may be controlled.

The BIB system 100 further includes a drain assembly 170 (shown in dashed lines), a spigot 150, and ventilation holes 190. The spigot 150 may be used to control the flow of gases and liquids into and out of the habitat through the drain assembly 170. The arrangement and location of the ventilation holes 190 may vary based on application of the BIB system 100, as will be described later. The ventilation holes 190 may be circular, oval, square or have other patterns and geometric shapes. There may be one or more rows of ventilation holes 190. The ventilation holes 190 may be arranged in a variety of patterns such as a circular pattern, a square pattern, a rectangular pattern, other shaped or random patterns and combinations thereof.

In the exemplary embodiment, the external box 110 is an outside tub or container made of acrylic material or other transparent material that allows light to permeate therethrough Likewise, the internal box 160 is an interior tub or container made of acrylic material or other transparent material that allows light to permeate therethrough. The external box 110 and the internal box 160 are configured to permit viewing of the interior up to 360°. In an exemplary embodiment, viewing is permitted 360°.

The internal box 160 is configured to be essentially fully received in the external box 110. The internal box 160 is configured as an interior container or tub that is removable or capable of being lifted out of the external box 110. In operation, the drain assembly 170 or spigot 150 may require cleaning. Therefore, the internal box 160 may be lifted and removed from the external box 110 before cleaning so the habitat (FIG. 2B) is not generally disturbed between cleanings and can be easily replaced back into the external box 110.

The drain assembly 170 is angled or has a V-shape so that liquid byproducts created in the habitat, such as compost tea (organic fertilizer) created by worms during a composting process, are directed to the spigot 150. Alternately, the drain assembly 170 may be U-shaped or sloped in a direction toward the spigot 150. The angled drain assembly 170 allows for drainage and collection of the liquid byproducts. The drain assembly 170 may be made of acrylic material or other transparent material that allows light to permeate therethrough. The transparent properties of the drain assembly 170 allows the drain assembly 170 to be visually inspected without the need to disturb, move, or lift the external box 110 or the internal box 160. In operation, the user has continuous visual inspection capabilities of both the habitat and, if desired, the drainage of the liquid byproducts (e.g., worm tea or compost tea) without the need to disturb the habitat and the drain assembly 170. The user simply needs to look through the drain assembly 170 to determine the level of liquid byproducts. The transparent properties minimize the disturbance of the habitat within the BIB system 100. In general, the internal box 160 would only need to be lifted to clean the drain assembly 170. The habitat may require water, liquid mixtures or other fluids from time to time. For example, the habitat may include vegetation that requires water, the water would also drain to the drain assembly 170.

FIG. 1B illustrates a Biome in a Box (BIB) system 100 in a blackout state in accordance with some exemplary embodiments of the present invention. FIG. 1D illustrates a blackout assembly 180 of the BIB system 100 of FIG. 1A-1B in accordance with some exemplary embodiments of the present invention. The lid 120, closing both the top of the external box 110 and the top of the internal box 160, is made of a dark or opaque material. Thus, the blackout assembly 180 or other outer panels, drapes, or curtains, when deployed, hang down vertically along the vertical side of the external box 110 and are used to simulate darkness within the habitat.

The blackout assembly 180 includes a skirt or drape 182 with an elastic band 183 at the top edge. The elastic band 183 is configured to hold the blackout assembly 180 up near or in proximity to the top edge of the external box 110. The skirt or drape 182 would drape around the spigot 150. The elastic band 183 would also allow the blackout assembly 180 to be place around the locking mechanism 130. In operation, a user may lift or open the blackout assembly 180 so that the habitat, internal box 160, and/or drain assembly 170 may be visually inspected. Once inspection is completed, the skirt or drape 182 may be released to fall under the force of gravity back along side of the external box 110.

FIGS. 1C and 1G illustrate an exploded view and a back view, respectively, of the external box 110 of the BIB system 100 of FIG. 1A in accordance with some exemplary embodiments of the present invention. The external box 110 includes a plurality of vertical side walls 112A, 112B, 112C and 112D. One or more of the vertical side walls 112A, 112B, 112C and 112D includes the ventilation holes 190. In the exemplary embodiment, ventilation holes 190 are in two side walls 112A and 112C. Nonetheless, the ventilation holes 190 may be placed in other walls or lid. The ventilation holes 190 allows for the ventilating of the habitat. Other ventilation holes (not shown) may be provided that would allow objects to expand beyond the BIB system 100, when necessary. The ventilation holes 190 need to be at a location that does not allow the soil or food waste to spill out. Furthermore, the ventilation holes 190 should not allow for water intrusion. The holes may be small to limit the size of external creatures that could enter (or exit) the system 100.

The bottom floor of the external box 110 includes the drain assembly 170. In other words, the bottom edges of vertical side walls 112A, 112B, 112C and 112D are not closed by a horizontally aligned bottom floor. The drain assembly 170 includes two plates 171A and 171B placed at an angle with respect to the other and with respect to side wall 112B and 112D such that a V-shaped bottom floor is formed. A bottom portion of side walls 112A and 112C serve as end walls for the drain assembly 170 or the V-shaped bottom floor. The apex A where the two plates 171A and 171B meet should be aligned with or just inside or above the bottom edges of the vertical side walls 112A, 112B, 112C and 112D so that the BIB system 100 is balanced and supported upright by the bottom edges of the vertical side walls 112A, 112B, 112C and 112D. The bottom portion of side walls 112A, 112B, 112C and 112D provide a skirt or enclosure around drain assembly 170.

The internal box 160 includes an irrigation tray 164, as best seen in FIGS. 1A and 1B, which is in air and fluid communication with the drain assembly 170. The two plates 171A and 171B are placed at an angle under the irrigation tray 164 to channel the flow of liquids and gases toward the spigot 150. The drain assembly 170 further includes a receptacle 174 in close proximity to the spigot 150 from which the spigot 150 may directly draw fluid and air therefrom. In some embodiments, ventilation holes 190 are placed below the irrigation tray 164 so that the drain assembly 170 is vented.

The receptacle 174 is represented by a squared cavity or well in proximity to side wall 112A, wherein the formation of the apex A is discontinued in close proximity to side wall 112A and a well is created. The side wall 112A in proximity to the receptacle 174 has an access port 118 formed therein. The access port 118 is configured to have a coupler 156 affixed in the access port 118. The coupler 156 may be a threaded nut or other fasteners configured to couple to a spigot, spout, hose, etc. The access port 118 also has coupled thereto the spigot 150 having a quick serve tap 152 via a valve lock bracket 154. The spigot 150 may be selectively turned on to dispense fluid byproducts from receptacle 174 through the access port 118. When the spigot 150 is turned off, the fluid byproducts cannot be dispensed.

As the drain assembly 170 is enclosed (but visible) under the internal box 160 and within the external box 110 so that children and others do not have easy access to the drain assembly 170 as some liquid byproducts (e.g., worm tea) can carry bacteria and other germs known to be harmful to humans.

Referring also to FIG. 1F, the lid 120 is hingedly coupled to a respective one of vertical side walls 112A, 112B, 112C and 112D. In an exemplary embodiment, the lid 120 is hingedly coupled to side wall 112B via hinge 135. Side wall 112B may be considered a back wall while side wall 112D is a front wall. The designation of the side walls as being front, back or end walls are only to provide a frame of reference for descriptive purposes.

Side wall 112D includes a first locking member 132. The lid 120 includes a second locking member 125 configured to mate with and latch to the first locking member 132. The first locking member 132 and the second locking member 125 are part of the locking mechanism 130. When the second locking member 125 is latched or in a locking state to the first locking member 132 a lock (not shown) would be fastened to the first locking member 132. The first locking member 132 and the second locking member 125 form a padlock hasp locking mechanism. Nonetheless, other lock arrangements may be substituted such as key hole locks, combination locking systems, voice activated locking systems, etc.

The lid 120 includes a top planar surface 122 and dependent sides 124 perpendicularly coupled to the edges of the top planar surface 122. When the lid 120 is closed, the dependent sides 124 are parallel to and positioned beside the exterior side of vertical side walls 112A, 112B, 112C and 112D.

Depending on the habitat, the lid 120 may be made in whole or part of transparent material so that when vegetation is growing, the growth cycle can be observed from the lid 12. However, during the composting process, if the lid 120 is transparent, the lid needs a blackout assembly to prevent or minimize light from permeating the lid's material.

Figure 1E:
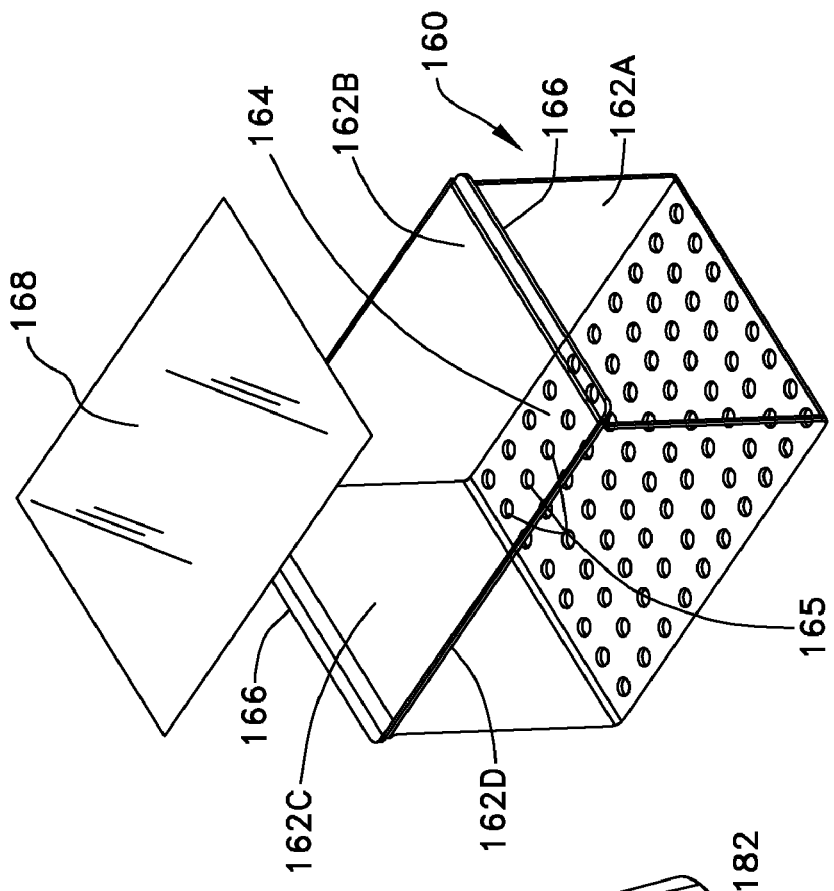
FIG. 1E illustrates the internal box of the BIB system of FIG. 1A with optional landscape paper in accordance with some exemplary embodiments of the present invention.
Figure 1D:
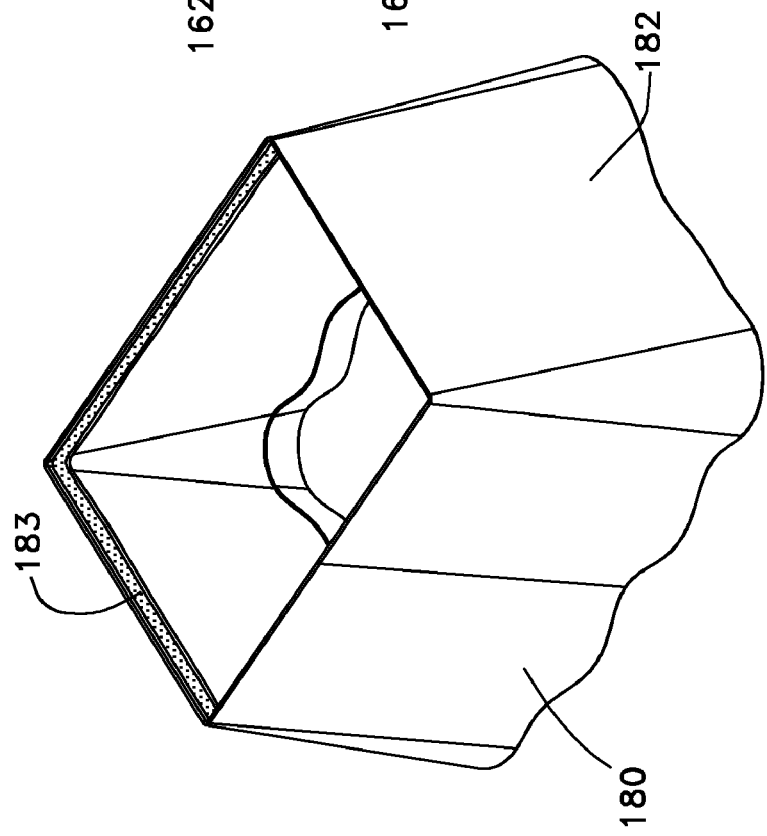
FIG. 1D illustrates a blackout assembly of the BIB system of FIGS. 1A-1B in accordance with some exemplary embodiments of the present invention.

FIG. 1E illustrates the internal box 160 of the BIB system 100 of FIG. 1A with optional landscape paper 168 in accordance with some exemplary embodiments of the present invention. The internal box 160 includes a plurality of vertical side walls 162A, 162B, 162C and 162D. The irrigation tray 164 is perpendicularly coupled to bottom edges of side walls 162A, 162B, 162C and 162D. The irrigation tray 164 includes a plurality of holes 165 which allow fluid and to drain therethrough.

In the exemplary embodiment, side walls 162A and 162C have handles or an overhang flanges 166 which is constructed and arranged to serve as handles when lifting the internal box 160 in and out of the external box 110. Furthermore, the handles or overhang flanges 166 serve to support or suspend the internal box 160 from the top edge of the external box 110. When the internal box 160 is installed, the handles or overhang flanges 166 are generally oriented at approximately 90 degrees with respect the top edge of side walls 162A and 162C. The handles or overhang flanges 166 rest on top of the top edge of side walls 112A and 112C of the external box 110 wherein when the internal box 160 is inserted, the entire box is substantially fully recessed and suspended or hung within the external box 110. The dependent sides 124 of lid 120 extends over the handles or overhang flanges 166 so that when the system 100 is outdoors, water intrusion from the lid is prevented from leaking into the internal box 160 and/or the external box 110.

The BIB system 100 may be a Compost-Biome in a Box or a WormWatcher configured for classroom, school use, gardening use or other personal use. The BIB system 100 incorporates several science and teaching units, such as, life and nutrient cycles, plant stages, human impact, soil and water quality to name a few. Equally important, the BIB system promotes "green" teaching. For example, the habitat is designed such that worms may compost or eat about three pounds of garbage per week and watching the worms eat and transform the garbage is entertaining. More important, effective composting would reduce approximately 23% to 34% of garbage thrown into our landfills. The habitat is relatively small so it can be put indoors or outdoors and is sealed so that inadvertent creatures in the soil will likely not escape. The system 100 is constructed and arranged to permit food waste or biowaste deposits to be added, as necessary, such as by unlocking and lifting of the lid 120. The lid 120 may have holes that are configured to be closed.

While not wishing to be bound by theory, landfills are known to provide anthropogenic methane emissions. It is commonplace to observe exhausts embedded in the landfill to allow the methane gas to escape into the atmosphere. Methane is considered 72 times more potent than CO2 over a 20-year time frame. Thus, a reduction of landfill matter by composting may serve to reduce methane emissions or greenhouse gas emissions.

Currently, food scraps, paper and/or other biodegradable products which form a consumer's garbage may be incinerated or placed in a landfill. Incinerators require energy and may burn coal for its operation which depletes additional environmental resources and creates pollution. Composting may reduce the volume of garbage needed to be incinerated or placed in a landfill to both protect the climate and restore soils.

As can be appreciated, the internal box 160 has a perforated floor (irrigation tray 164) and the external box 110 is fitted with a spigot 150. By placing the worms in the internal box 160 with garbage, such as paper products, kitchen scraps, and other waste, the created byproducts include solid byproducts such as worm castings (nutrient enriched top soil) and liquid byproducts such as "compost tea" that filters through the perforated floor into the drain assembly 170 where liquid byproducts can be combined with water or other mixtures for use as a rich organic fertilizer. Similarly, the top soil in the habitat may be removed and used the internal box.

When the system 100 is used as a Compost-Biome in a Box, a worm farm may be created. The worm farm will operate most efficiently in temperatures between 45 and 85 degrees Fahrenheit. Thus, the system 100 may be used indoors during winter and outdoors during spring and summer. In general, the earthworms work in darkness. Thus, to observe the earthworms in action, the observers can peak behind the curtain or drape of the blackout assembly 180. And, earthworms can survive with one feeding for up to six to eight weeks making the Compost-Biome in a Box system a pet-friendly and pet-owner friendly habitat. The system may be used to grow at least one edible food source (habitat) while simultaneously receiving garbage for composting so as to reduce the amount of garbage sent to landfills; and/or generate a fertilizer. The system 100 may be made larger or smaller depending on the application.

In operation, the internal box 160 may be lined with landscape paper 168 (FIG. 1E) or one or more layers of newspaper. After, the perforated floor (irrigation tray 164) is lined, such as with landscape paper 168, peat moss and composting manure may be added. Thereafter, worms may be added. After the worms are added, the lid 120 is shut and the blackout assembly 180 installed.

Other products that may be used include composting substances, potting mixtures, soil and/or other biodegradable or organic substances.

In view of the foregoing, the BIB system 100 is constructed and arranged to demonstrate the creation of compost tea or worm tea in accordance with some exemplary embodiments of the present invention.

The BIB system 100 is constructed and arranged to allow observers, such as students, teachers and/or others, to observe earthworms breaking down food waste or biowaste into worm castings (solid byproducts).

The BIB system 100 is constructed and arranged to allow observers, such as student teachers and/or others, to observe a full circle or cycle of composting.

The BIB system 100 is constructed and arranged to allow observers, such as student teachers and/or others, to plant seeds in the internal box 160 by dropping or inserting seeds through access ports such as the lid 120. The seeds are then left to grow in the internal box 160 so that the growth cycle of vegetation and other plant life can be observed.

The BIB system 100 is constructed and arranged to dispense therefrom a portion of the worm tea, compost tea or by liquid product produced by the composting process taking place in the internal box 160.

The BIB system 100 is constructed and arranged to have a particular amount of air or oxygen or air/oxygen ventilation for the volume of space in the internal box 160.

The BIB system 100 includes an outer container (external box 110) and an inner tub (internal box 160), the inner tub being configured to be lifted out from the outer container for cleaning of the drain assembly or change of the habitat.

The BIB system 100 may be provided with an amount of soil and earthworms. Additionally, frogs and lizards may also be provided in the habitat. The BIB system 100 includes access ports to add paper items (e.g., junk mail, newspapers, etc.), food waste and/or biowaste to feed the earthworms as the composting process takes place (meaning the breakdown into worm castings) to create a fertilized soil bed to grow vegetation or other plant life. In one exemplary embodiment, the access ports may include air holes. In another exemplary embodiment, the access port may include lids.

In operation the full circle composting process includes adding food waste or biowaste in the internal box 160 so that earthworms break down the food waste or biowaste into worm castings. After a fertile bed is created, seeds may be planted in the fertile bed by dropping seeds through the lid 120 or dome, the dome will be described in more detail later.

Figure 2A:
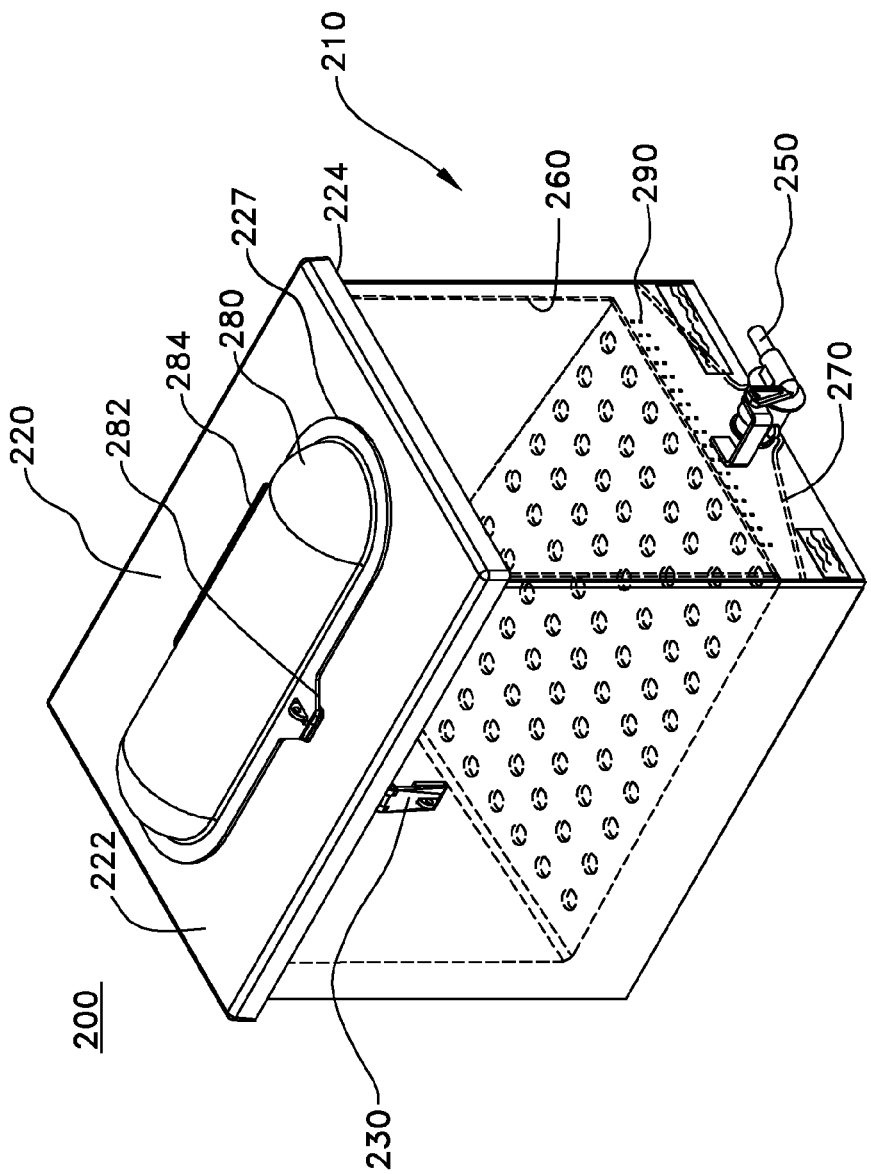
FIG. 2A illustrates another BIB system in accordance with some exemplary embodiments of the present invention.

The full circle composting process further includes watching the germination and growth of the vegetation from the plant seeds. The vegetation would also tend to move or migrate toward artificial or natural light. The access ports may provide a source of light in the lid 120 of the system 100. For dome shaped access ports, the vegetation may be seen through such access ports (FIG. 2A).

The byproducts of the composting process by the earthworms also generate a liquid byproduct known as worm tea or composting tea. This tea is a liquid fertilizer that can be used in gardens or on plants in pots. The tea can be dispensed from a drain assembly 170 to the spigot 150.

The blackout assembly 180 of the BIB system 100 is optional. For example, the BIB system 100 may be used for creating and/or studding a habitat. The BIB system 100 includes a container (external and internal boxes 110 and 160) made of transparent walls configured to house therein a habitat or ecosystem. The habitat may include one or more of water, sand, soil, composite, rocks, plants, animals, worms, frogs, bugs, light, etc. The habitat for each animal, worms, frogs, bug, biotic, etc. may be different depending on the specific species and preferred environment. The transparent walls of the container(s) allows the students, children or others (such as adults and teachers) to view the habitat, animals, worms, frogs, bugs, biotic, etc. from many angles and locations)(360°. The habitat may include one or more living and/or non-living components. For example, the habitat may include a non-living component (such as, moisture indicator), water, sand, soil, compost, air, other abiotic matter and/or combinations thereof. The habitat is configured to support living (biotic) or once living organisms which may be simple, complex, single celled or multi-celled.

The hinged lid 120 (or any other access panel) may include a lock or other access control mechanism to limit or restrict access to the habitat or the interior of the external box 110 or internal box 160.

The locking mechanism is configured to restrict access through the use of a locking device or other access control mechanism. The lock or access control mechanism may be controlled by the teacher or other designated administration control person or by others. The lock or access control mechanism may limit access by students, children or others.

The lockable feature keeps children or others, not skilled in or not authorized to perform the care of the habitat, animal, worms, frogs, ecosystem, etc., from accessing the inside of the boxes without permission. The access control/locking mechanism may be electronic, voice activated, pin activated, key activated, and other electro-mechanical combinations to allow the hinged door, panel, or lid to open. The access control mechanism may include a biometric sensor to limit or control access to the interior of the container.

The system 100 is configured to be lightweight and portable. For example, the container may be a habitat, terrarium, biotope or the like. The weight of the BIB system 100 may permit transporting creatures or habitat, animals, etc., easily from class to class or classroom to home or from place to place. The BIB system may include handles or grips so as to simplify transporting.

FIG. 2A illustrates another BIB system 200 in accordance with some exemplary embodiments of the present invention. The BIB system 200 includes an external box 210, lid 220, internal box 260 (shown in dashed lines) and blackout assembly (e.g., blackout assembly 180). In the exemplary embodiment, the external box 210 is configured to receive the internal box 260. The lid 220 covers and encloses the top opening of the external box 210 and the top opening of the internal box 260. The lid 220 includes a locking mechanism 230 so that access to the interior of the BIB system 200 may be controlled. The BIB system 200 further includes a drain assembly 270 (shown in dashed lines), a spigot 250, and ventilation holes 290.

The system 200 is similar to system 100. However, system 200 includes an access port 227 formed in the planar surface 222. The lid 220 includes a top planar surface 222 and dependent sides 224 perpendicularly coupled to the edges of the top planar surface 222. The access port 227 is configured to be closed by an auxiliary lid 280. In the exemplary embodiment, the auxiliary lid 280 has a dome shape. The auxiliary lid 280 is hingedly coupled to planar surface 222. The auxiliary lid 280 is also configured to have access controlled through a locking mechanism 282.

FIGS. 2B and 2C illustrate an end view of the BIB system of FIG. 2A with a habitat H or biome shown in FIG. 2B. The access ports are covered or enclosed by at least one dome (e.g., auxiliary lid 280) made of transparent material. The domes may have ventilation holes. The access ports provide a source of light into the container/tub through the lid. The vegetation V in the habitat H will tend to migrate to the source of light. While not wishing to be bound by theory, the vegetation V may grow over time through the access ports and thus would be visible in the dome (e.g., auxiliary lid 280). The auxiliary lid 280 may be locked via locking mechanism 282 configured as a padlock hasp assembly. The auxiliary lid 280 may be pivoted open via hinge 284 so that more air may flow in and out of lid 220 while lid 220 remains locked by a locking mechanism 230.

Furthermore, the access port 227 includes a recessed perimeter area 227A and an aperture 227B. The auxiliary lid 280 is made of transparent material so that sunlight may shine therethrough. The auxiliary lid 280 when closed is mounted such that air flows under the lid into the recessed perimeter area 227A and into the aperture 227B. Likewise, air flows up through the aperture 227B, through the recessed perimeter area 227A and under the lid so that some gases may escape from the habitat H (FIG. 2B).

The lid 280 may be mounted in a manner that allows air to flow around the perimeter edge when the lid 280 is closed.

The habitat H includes soil S or other biodegradable material, worms W and vegetation V. In the exemplary embodiment, the habitat H is created in the internal box 260. Any tea flowing through the irrigation tray 264 flows to the drain assembly 270. Ventilation holes 290 are position below the irrigation try 264 and in the area of the drain assembly 270.

FIG. 3A illustrates yet another BIB system 300 in accordance with some exemplary embodiments of the present invention wherein FIG. 3B illustrates an exploded view of the BIB system 300 of FIG. 3A. The BIB system 300 includes an external box 310, lid 320, internal box 360 and support base 340. An optional blackout assembly (e.g., blackout assembly 180) may be provided. In the exemplary embodiment, the external box 310 is configured to receive the internal box 360. The lid 320 covers and encloses the top opening of the external box 310 and the top opening of the internal box 360.

The lid 320 is also shown without a hinge. Therefore, when opening the lid 320, the lid 320 is lifted and set aside instead of being rotated. Nonetheless, the lid 320 may include a lid such as lid 120 or lid 220 described above with one or more hinges.

The BIB system 300 further includes a drain assembly 370, a spigot 350, and ventilation holes 390. The spigot 350 may be used to control the flow of gases and liquids into and out of the habitat through the drain assembly 370. The arrangement and location of the ventilation holes 390 may vary based on application of the BIB system 300.

The external box 310 and the internal box 360 are configured to permit viewing of the interior up to 360°. In an exemplary embodiment, viewing is permitted 360°. Both the external box 310 and internal box 360 are transparent and may be made of clear plastic, acrylic material, glass, or other transparent materials. The internal box 360 is essentially the same as internal box 160 of FIG. 1A. However, the bottom end of the external box 360 is configured to be cradled or nested in the support base 340.

The support base 340 includes a V-shaped floor having first and second angled floor sides 341A and 341B. The support base 340 further includes base side walls 344A, 344B, 344C and 344D. Base side wall 344A has a groove formed therein for receipt of the spigot 350. In the exemplary embodiment, the base side wall 344A is sloped downward in the direction of the groove from the outer edges.

The base side walls 344B, 344C and 344D have a height which approximates or does not exceed the depth of the drain assembly 370. Therefore, when the internal box 360 is cradled in the support base 340, the complete volume or nearly complete volume of the internal box 360 is not obstructed.

The drain assembly 370 includes two plates 371A and 371B placed at an angled or have a V-shape so that the compost tea is directed to the spigot assembly 350. The angled drain assembly 370 allows for drainage and collection of compost tea (fertilizer). The drain assembly 370 may be made of glass, clear plastic, acrylic material, or transparent material that allows light to permeate therethrough or other materials that are opaque.

The bottom floor of the external box 310 extends down below the bottom edges of the vertical side walls of the external box. The angle of the two plates 371A and 371B track the slope or angle of the floor sides 341A and 341B in the support base 340.

In an alternate exemplary embodiment, the external box 310 may be omitted wherein the internal box 360 becomes the external box. The support base 340 would be configured to adapt or be modified to the new size of the internal box 360. The support base 340 may be made of rubber, hard plastic or other materials. The support base 340 may be opaque and/or lightweight.

Furthermore, the base may be a frame structure that reduces the amount of material needed for the base and may include support columns, beams or equivalent. As can be appreciated, removing one of the boxes reduces materials.

The BIB systems described herein may substitute a different internal box for the different habitats needed. For example, if the habitat is an aquarium, the internal box may be omitted. On the other hand, the external box and internal box would be substituted with a box with a horizontal floor without or without holes.

Figure 4:
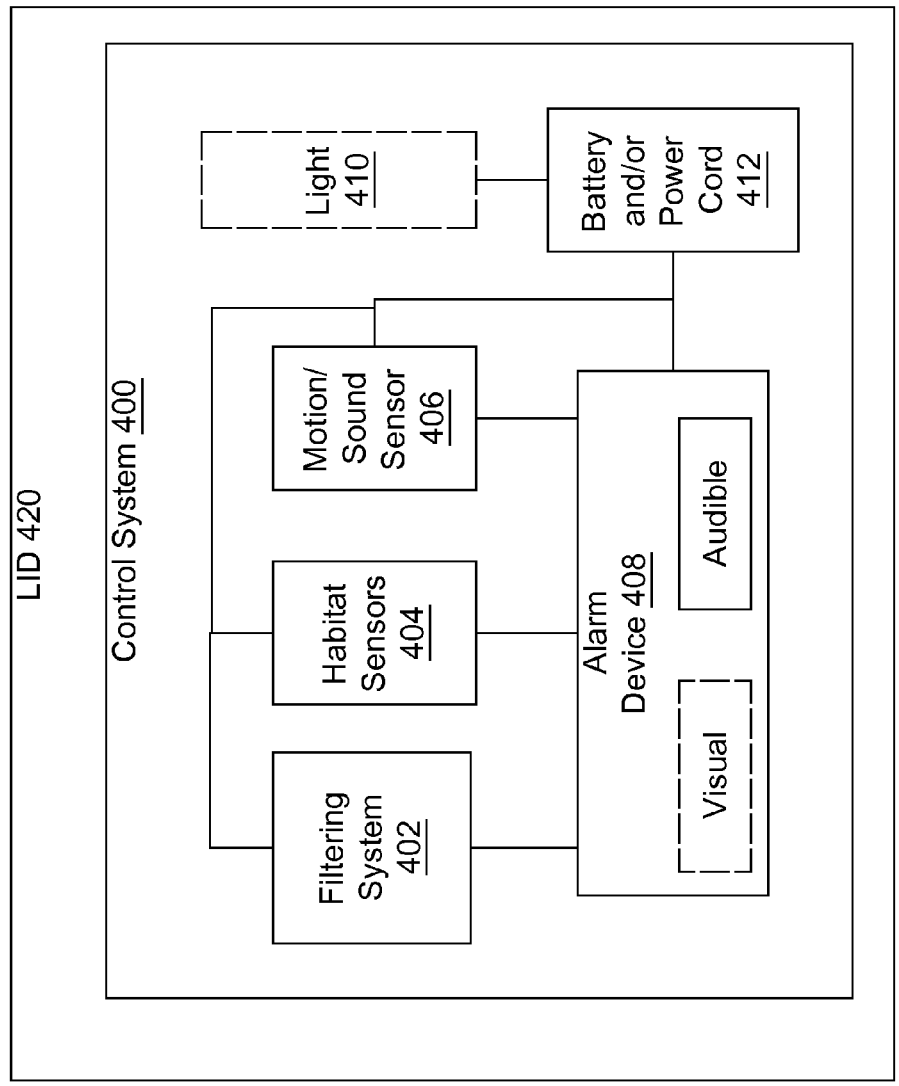
FIG. 4 illustrates a block diagram of a lid with a control system in accordance with some exemplary embodiments of the invention.

FIG. 4 illustrates a block diagram of a lid 420 with a control system 400 in accordance with some exemplary embodiments of the invention. The control system 400 may include a lights 410, habitat sensors 404 such as to sense and read the temperature or other environmental (e.g., humidity, temperature, movement/motion, etc.) parameters of the habitat. The control system 400 may include a filtering system 402, motion/sound sensors 406 and an alarm device 408. The control system 400 includes a battery or a power cord 412 to power the electronics. The battery source, if provided, may be rechargeable.

While not shown, the control system 400 may include a voice responsive module to control one or more features of the habitat or provide readings from one or more the sensors. The control system 400 may provide audio output to describe the habitat and/or creature.

The motion/sound sensor 406 may be configured to detect one or more parameters. For example, the motion/sound sensor 406 may detect activity (motion or sound) in the container, activity (movement or sound) out of the container or boxes, and/or whether the creature(s) or animal(s) are alive or dead. The motion/sound sensor 406 may be configured to detect how many creatures, animals, etc. are moving in the container or boxes and provide a visual reading of such detection or indication.

The alarm device 408 may be configured to generate a feeding schedule alarm and may be visual or audible. The feeding schedule alarm is configured to notify children, students, teachers, or others when to feed the animal, worms, frogs, creature, etc. on a pre-set feeding schedule or periodic basis. Thus, one or more control buttons, keypads or other means to enter a setting for sounding a feeding schedule alarm, or a feeding schedule may be provided. A display may be included to display one or more of the feeding schedule, temperature, other sensed environmental parameters, etc.

The motion/sound sensors 406 may be used by the alarm device 408 to alert students, children, adults, teachers and/or others when the lid is opened.

The power cord, if provided, is configured to plug in to an outlet available in a school, building or residence. The power will power the control system elements or components. The filtering system 402 may be affixed to the container wall or, alternately, the lid. The light 410 would provide illumination in the internal box. Various types of artificial as well as natural light may be needed.

A processor and memory may be provided to log individuals based on their biometrics. For example, the BIB system may be configured to automatically log in the identity of a student when the student is sensed by the biometric sensor to later validate whether the student has performed a particular task or to log those entering, feeding, performing maintenance, etc.

Access may be provided based on a stored profile, such as identity of the user, a feeding schedule for the creature, times of day, proximity of other biomes, an experiment, maintenance and set-up, modifications in the habitat, adjustment of the habitat, etc.

The lid 420 may be opaque for aesthetic purposes such as to hide components of control system 400. The lid 420 may have no openings between the lid and the top edge of the boxes to minimize spills during transport, protect the creatures, animals, worms, frogs, etc. and/or prevent students from adding materials (e.g., liquid/solids or contaminants) to the habitat that may harm the creatures, animals, worms, frogs, biotic, etc. However, depending on the habitat and creature, animal, worms, frogs, etc., air holes in the lid may be provided or other controlled air infusion may be supplied.

Figure 5:
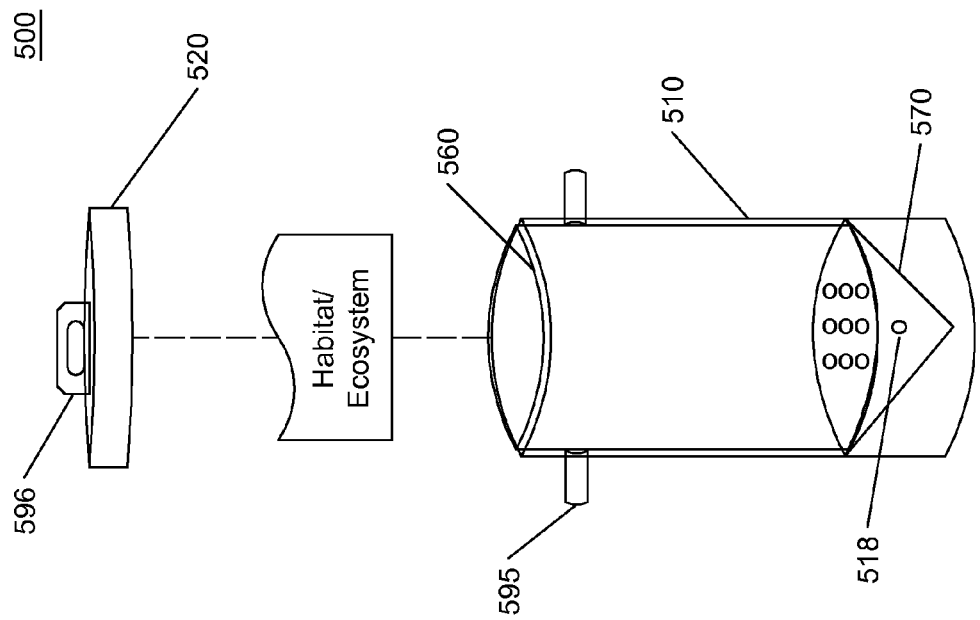
FIG. 5 illustrates an exploded view of a cylindrically-shaped BIB system in accordance with exemplary embodiments of the invention.

FIG. 5 illustrates an exploded view of a cylindrically-shaped BIB system 500 in accordance with exemplary embodiments of the invention. The BIB system 500 includes a cylindrically-shaped external box 510 and internal box 560. The drain assembly 570 would have a generally conical shape with an access port 518. The access port 518 would have a spigot (FIG. 1A) attached.

In FIG. 5, the external box 510 is shown with side handles 595. Furthermore, lid 520 is shown with a handle 596. In this embodiment, a habitat is added into the internal box 510 for composting, vegetation growth, etc.

Figure 6:
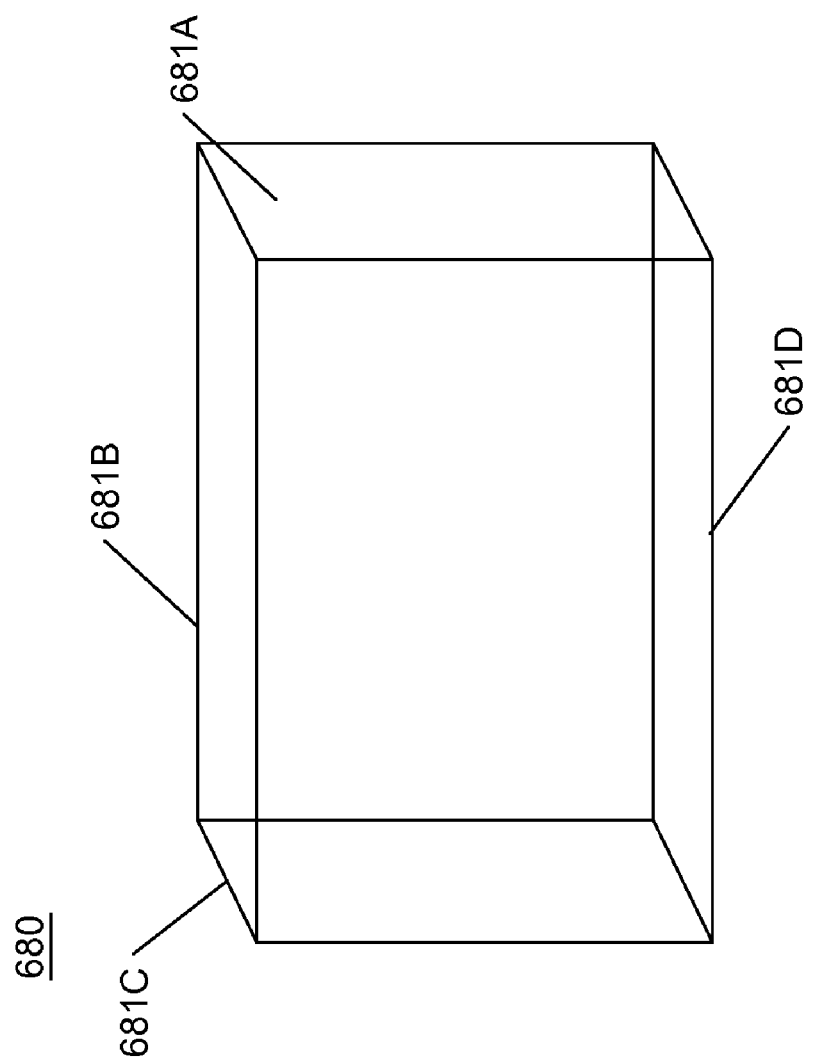
FIG. 6 illustrates a sleeve in accordance with some exemplary embodiments of the invention.

FIG. 6 illustrates a sleeve 680 in accordance with some exemplary embodiments of the invention. The blackout assembly 180 may be substituted with a sleeve 680 that is configured to receive therein the external box 110. The sleeve 680 may be black and/or opaque to simulate below-ground, underground or night depending on the particular biotic. The sleeve 680 includes four sleeve panels 681A, 681B, 681C and 681D. One or more of the four sleeve panels 681A, 681B, 681C and 681D may be slideable to open up to the external box to expose the interior compost process or habitat.

In sleeve 680 is shown as a separate element that would be placed around or concentric to the external box. However, the sleeve 680 may be integrated with the external box. For example, a channel may be made around the external box that would receive a bottom end of the sleeve 680 and support the sleeve so that the sleeve and external box are concentric. The sleeve may be lifted when observation or light is desired.

Figure 7:
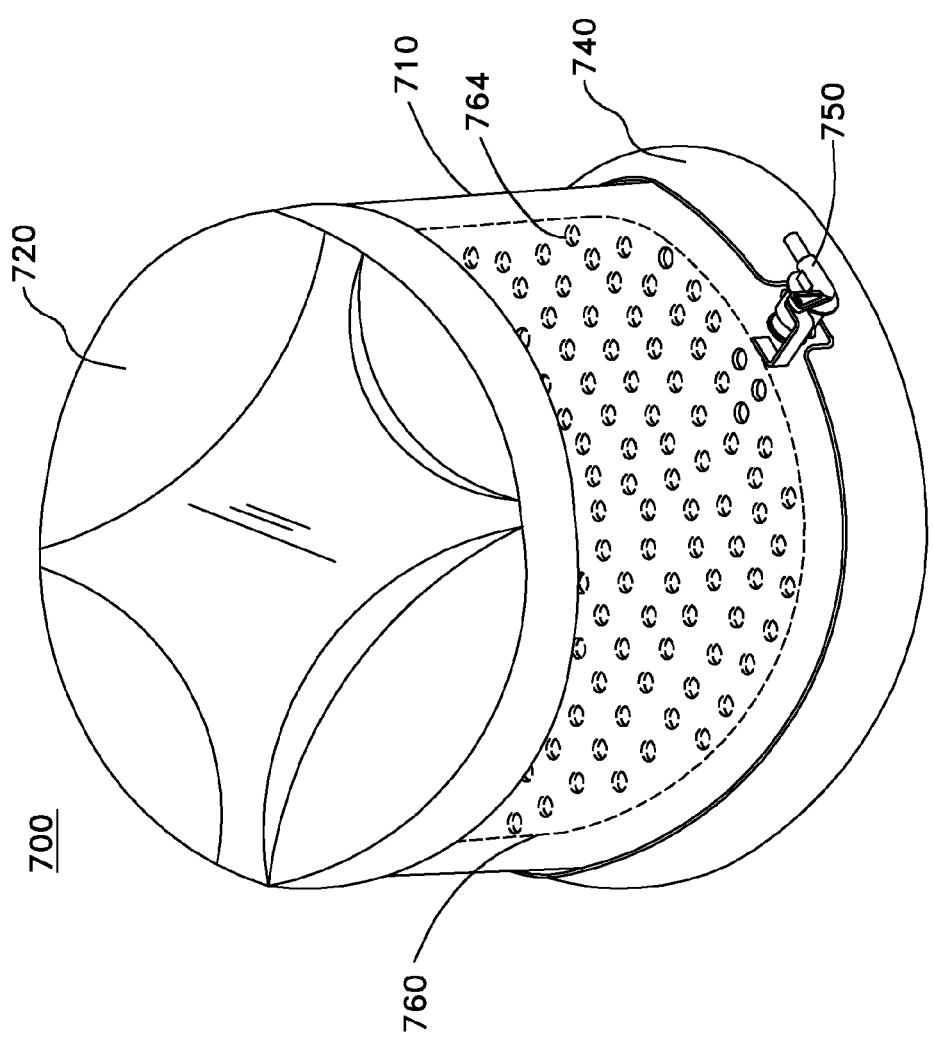
FIG. 7 illustrates yet another BIB system in accordance with some exemplary embodiments of the present invention.

FIG. 7 illustrates yet another BIB system 700 in accordance with some exemplary embodiments of the present invention. The BIB system 700 includes an external box 710, lid 720, internal box 760 and support base 740. In the exemplary embodiment, the external box 710 is configured to receive the internal box 760, both of which are cylindrically-shaped. The support base 740 is dimensioned to fit the size of the external box 710. The base 740 should support the drain assembly or provide a receiver to capture fluid byproducts or other byproducts from the internal box 760. In such an embodiment, the materials of the drain assembly may be omitted. The lid 720 covers and encloses the top opening of the external box 710 and the top opening of the internal box 760.

The lid 720 is also shown without a hinge. Therefore, when opening the lid 720, the lid 720 is lifted and set aside instead of being rotated. Nonetheless, the lid 720 may include one or more hinges and may include a locking mechanism.

The BIB system 700 further includes a drain assembly (not shown) and a spigot 750. The system 700 may include ventilation holes (not shown). The spigot 750 may be used to control the flow of gases and liquids into and out of the habitat through the drain assembly. The bottom floor of the internal box 760 has holes 764 or perforations to allow fluid byproducts or other byproducts to escape to the drain assembly.

Additionally, the surface of one or more of the side walls may be painted, tinted, coated or have a paper or lining applied thereto to simulate darkness.

The surface of one or more side walls may include a background, image, graphic design or picture that would match or complement the habitat surrounding.

The materials described herein can be man-made (e.g., synthetic) or natural (but more likely man-made). The material may include an environmentally "green" material, polyethylene or other materials (i.e., natural and/or man-made).

In view of the foregoing, the BIB systems may include at least one magnification window (not shown) on the external box, internal box or lid. The magnification window may include a built-in lens to allow students to observe creatures/habitat using magnification. The one or more magnification windows may be provided. For example, one or more side walls may include or provide a separate magnification window. Alternately, just a portion of a side wall of the external box and/or internal box may be made of a material with magnification properties. The lid may include a magnification window. For example, the dome (FIG. 2A) may include a material with magnification properties. Alternately, the dome may be replaced with a plate with no curvature wherein the plate would have magnification properties.

The BIB system may further include a periscope system (not shown) or microscope system (not shown). The magnification window may include a lens with a concaved shape, convexed shape or other shape of a lens suitable for magnifying objects observed therethrough.

The term box may include various shapes and should not be limited to a square or rectangle geometric shape. The term box is a container, tub or enclosure.

The external box and the internal box may be cylindrically-shaped, rectangularly-shaped, square-shaped other geometrical shapes and combinations thereof.

In view of the foregoing, the biome in a box system comprises a transparent external container having a first size and a top edge and a transparent internal container having a second size configured to fit within the external container. The internal container has at least one handle configured to hang over and suspend from the top edge of the external container. The system further includes a lid having a side wall extending over the at least one handle and the top edge and a drain assembly under the transparent internal container.

While the present invention has been described with respect to various features, aspects, and embodiments, those skilled and unskilled in the art will recognize the invention is not so limited. Other variations, modifications, and alternative embodiments may be made without departing from the spirit and scope of the present invention.

What is claimed is:

1. A biome in a box system comprising:
   a transparent external container having a first size and shape and a top edge;
   a transparent internal container having a second size and shape configured to fit within said external container, the internal container for placement of a habitat and having at least one handle configured to hang over and suspend from the top edge of the external container;
   a hinged lid having a side wall extending over the at least one handle and the top edge;
   a drain assembly positioned under the transparent internal container;
   wherein the lid includes an access port and is made of opaque material, and wherein the access port includes a dome made of transparent material, wherein the lid and dome are separately lockable and openable.

2. The system according to claim 1, wherein the lid includes an access port and is made of opaque material.

3. The system according to claim 1, wherein the lid is mounted to the external container, provides ventilation and minimizes water intrusion into the habitat.

4. The system according to claim 1, further comprising a blackout assembly selectively coupled around the transparent external container.

5. The system according to claim 4, wherein the blackout assembly includes one of a skirt or sleeve.

6. The system according to claim 1, wherein the transparent internal container is removable and comprises a perforated bottom floor configured to communicate fluid from the transparent internal container to the drain assembly.

7. The system according to claim 1, wherein drain assembly is configured to direct the fluid to a spigot coupled to the transparent external container.

8. The system according to claim 7, wherein the drain assembly is transparent, has a V-shape and a first end, in proximity to the spigot, having a well from which the spigot draws the fluid.

9. The system according to claim 8, wherein the transparent external container includes ventilation holes to ventilate the drain assembly.

10. The system according to claim 7, further comprising a base having a cradle conforming to a shape of the drain assembly, the base being configured to support the drain assembly and the transparent external container.

11. The system according to claim 1, wherein the transparent external container and the transparent internal container are one of cylindrically-shaped, rectangularly-shaped, square-shaped, and combinations thereof.

12. A biome in a box system comprising:
a transparent external container having a top edge;
a transparent internal container for placement of a habitat and having at least one handle being configured to hang over and suspend from the top edge of the external container;
a lockable lid having a side wall extending over the at least one handle and the top edge; and
a transparent drain assembly having a V-shape and being coupled to the transparent external container at a location under the transparent internal container, wherein the lid includes an access port and the access port includes a dome made of transparent material, wherein the lid and dome are separately lockable and openable.

13. The system according to claim 12, further comprising a blackout assembly selectively coupled around the transparent external container.

14. The system according to claim 12, wherein the transparent internal container is removable and comprises a perforated bottom floor configured to communicate fluid byproducts from the transparent internal container to the drain assembly.

15. The system according to claim 14, wherein the drain assembly is configured to direct the fluid byproducts to a spigot coupled to the transparent external container; and the drain assembly comprises a first end, in proximity to the spigot, having a well from which the spigot draws the fluid byproducts.

16. The system according to claim 12, further comprising a base having a cradle conforming to a shape of the drain assembly, the base being configured to support the drain assembly and the transparent external container.

17. The system according to claim 12, wherein the transparent external container and the transparent internal container are cylindrically-shaped, rectangularly-shaped, square-shaped, and combinations thereof.

\* \* \* \* \*